United States Patent [19]

Venkatasetty

[11] Patent Number: 5,746,900
[45] Date of Patent: May 5, 1998

[54] NON-AQUEOUS AMPEROMETRIC MULTI-GAS SENSOR

[75] Inventor: H. V. Venkatasetty, Burnsville, Minn.

[73] Assignee: H.V. Setty Enterprises, Inc., Burnsville, Minn.

[21] Appl. No.: 925,684

[22] Filed: Sep. 9, 1997

Related U.S. Application Data

[63] Continuation of Ser. No. 612,319, Mar. 7, 1996, abandoned.

[51] Int. Cl.$^6$ .................................................. G01N 27/26
[52] U.S. Cl. .................................... 204/415; 204/412
[58] Field of Search ........................... 204/412, 415, 204/431, 432; 422/82.04, 83

[56] References Cited

U.S. PATENT DOCUMENTS

| | | | |
|---|---|---|---|
| 4,521,290 | 6/1985 | Venkatasetty | 204/412 |
| 4,522,690 | 6/1985 | Venkasetty | 204/1 T |
| 4,595,486 | 6/1986 | Schmidt et al. | 204/412 |
| 4,622,996 | 11/1986 | Venkatasetty | 204/1 T |
| 4,851,088 | 7/1989 | Chandrasekhar et al. | 204/1 T |
| 4,948,490 | 8/1990 | Venkatasetty | 204/412 |
| 4,988,429 | 1/1991 | Matthiessen | 204/415 |
| 5,223,353 | 6/1993 | Ohsawa et al. | 429/192 |
| 5,547,554 | 8/1996 | Kiesele | 204/415 |

OTHER PUBLICATIONS

Chul Park[a], Dong Hyun Yun[a], Sung-Tae Kim[a], Yung Woo Park[b], "Enhancement of the $NO_2$–Sensing Capability of Copper Phthalocyanine by Measuring the Relative Resistance Change", Sensors and Actuators B 30 (1996) 23–27, 1996 Elsevier Science S.A., no month available.

*Primary Examiner*—Bruce F. Bell
*Attorney, Agent, or Firm*—Haugen and Nikolai, P.A.

[57] ABSTRACT

A versatile, selective and sensitive non-aqueous electrochemical amperometric gas sensing devices of great sensitivity are disclosed which operate in a redox voltage range from about −3 to about +2.5 V and exhibit long term stability over a wide temperature range.

17 Claims, 16 Drawing Sheets

$$\text{SAMPLING RATE} = D \frac{A}{d}$$

$$= 0.04 \; \frac{cm^2}{SEC} \; \frac{5 \, cm^2}{0.5 \, cm} \; \frac{60 \, SEC.}{MIN.}$$

$$= 25 \; cm^3/MIN.$$

$$\text{RESPONSE TIME} = \frac{d^2}{D} = 8 \; \text{SECONDS}$$

NON-AQUEOUS AMPEROMETRIC MULTI-GAS SENSOR

This is a continuation of application Ser. No. 08/612,319, filed on Mar. 7, 1996, now abandoned.

The government may have certain rights in this invention pursuant to a Small Business Innovative Research (SBIR) grant from the National Science Foundation No. DMI-9461112.

BACKGROUND OF THE INVENTION

I. Field of the Invention

The present invention relates generally to electrochemical measurements of the concentration of one or more species of interest in a mixture, of gases and, more particularly, to non-aqueous amperometric multi-gas sensor for the detection and monitoring of toxic gases and toxic organic solvents and vapors.

II. Related Art

It is well known that most metallic ions, gases and organic compounds and vapors undergo electrochemical oxidation and/or reduction at the surface of noble metal electrodes at appropriate voltages characteristic of the chemical species. This phenomenon has been used to construct cells for the qualitative or quantitative determination of such species. However, an electrochemical cell containing these electrodes needs to be housed in a suitable electrolyte medium which acts as a sink for the molecules of the chemical species of interest to dissolve and diffuse to the working or sensing electrode and undergo redox reaction when the necessary voltage is applied.

The limiting current ($i_L$) generated in the cell due to this reaction is proportional to the concentration (C) of the chemical species. The relationship between the diffusion current and the concentration is given by:

$$i_L = \frac{nFAD}{d} C$$

where n is the number of electrons transferred in the reaction, F is the Faraday constant, A is the electrode area, D is the diffusion coefficient for the chemical species and d is the diffusion layer thickness.

Conventional aqueous acid or basic type electrolyte based electrochemical sensors have a relatively high vapor pressure of about 20 mm of Hg at room temperature; they also have very limited operating life of about six months and have unstable baseline. These electrolytes are corrosive and toxic. These sensors with noble metal electrodes normally have a limited voltage range of about 1.23 Volts, the thermodynamic decomposition potential of water, and therefore sensors with aqueous electrolytes are not able to detect gases like carbon dioxide and most organic chemical species whose redox potentials are well above the decomposition potential of water.

Sensors using non-aqueous electrolytes have also been in use for some time, for example, to sense the presence of carbon monoxide (CO) and other toxic gases such as nitrogen oxides ($NO_x$) in the environment. Examples of such systems are found in U.S. Pat. No. 4,522,690 to H. V. Venkatasetty, the inventor in the present application, which discloses the use of a non-aqueous aprotic (without available hydrogen ions) electrolyte of lithium perchlorate ($LiClO_4$) in a solvent selected from propylene carbonate (PC) and γ-butyrolactone (γ-BL) with a minor amount of polyethylene oxide (PEO). Another patent to H. V. Venkatasetty, U.S. Pat. No. 4,521,290, utilizes a non-aqueous aprotic organic based solvent solution of γ-BL, PC or N, N' dimethylformamide (DMF) with an electrolyte salt selected from lithium perchlorate and tetraalkylammonium perchlorates. Other references to non-aqueous systems in which H. V. Venkatasetty is an inventor or co-inventor, and which provide additional background, include U.S. Pat. Nos. 4,851,088; 4,948,490; and 4,622,996. Of these, U.S. Pat. No. 4,948,490 discloses an environmental sensor which includes an amount of tetraalkyl ammonium salt in one or more aprotic solvents in a polymeric based solid electrolyte film.

A further reference (U.S. Pat. No. 4,595,486) to Schmidt et al discloses a non-aqueous electrochemical gas sensor for detecting a gas constituent such as hydrazine. That system utilizes a 3-electrode amperometric system and an electrolyte system which includes n-methyl-2-Pyrrolidone as the solvent and contains a tetraalkylammonium salt.

Whereas, progress has been made in the area of non-aqueous electrolyte solution based gas sensor technology, most of these sensors are dedicated to the detection of a single species of interest or are limited to detecting species within a rather narrow generally low redox voltage range. These devices also tend to lack accuracy at low concentration. There remains a definite need for a system that covers a wide redox voltage range which also exhibits long term stability over a wide temperature range which has the sensitivity to detect species of interest at relatively low concentrations.

SUMMARY OF THE INVENTION

By means of the present invention, very versatile, non-aqueous electrochemical amperometric gas sensing devices of great sensitivity have been developed capable of detecting gases having a wide range of redox potentials, many at very low concentrations. The system will detect oxygen and carbon dioxide, and very low concentrations (in the range of 10 to 100 PPM) of species including ammonia ($NH_3$), hydrogen sulfide ($H_2S$), sulfur dioxide ($SO_2$) and nitrogen dioxide ($NO_2$) and organic vapors such as trichloroethylene. The device will detect 200 to 1000 PPM of carbon tetrachloride and 100 PPM of dichloromethane, tetrachloroethylene, chloroform, n-butanol, and methanol.

Non-aqueous electrolyte solutions on which the sensor technology is based developed by this invention are useful throughout a wide redox voltage range from about −3 to +2.5 Volts. These electrolytes have very low vapor pressures of, for example, (about) 0.03 mm of Hg at room temperature and therefore the sensors operate well over two years with a stable baseline. The electrolytes also have relatively high boiling points (>200° C.) and low freezing point ($^{18}$ −40° C.). Most gases and organic vapors are more soluble (typically by an order of magnitude) in non-aqueous electrolytes and therefore, very low concentrations of these chemical species can be detected and the sensors can operate over a wide temperature range. Using the technique of scanning voltammetry and a time variable sampling rate with microprocessor controlled electronics, these sensors can be "Intelligent" sensors capable of self diagnostics and capable of multi-gas sensing at low concentrations.

The sensor of the invention is based on one unique non-aqueous electrolyte system that has been developed and successfully demonstrated in laboratory cells and prototype cells for the detection of toxic gases and organic chemical species. The preferred electrolyte systems of the invention include solutions of tetraalkylammonium salts in pure ternary or quaternary solvent mixtures of aprotic solvents. The preferred aprotic solvents from which the preferred mixture constituents are selected include γ-butyrolactone, propylene carbonate, ethylene carbonate, dimethoxy ethane, dimethyl carbonate, ethyl acetate and diethyl carbonate and other aprotic species. The preferred ternary solvent mixtures includes mixtures of propylene carbonate (PC), gamma butyrolactone (γ-BL) and ethylene carbonate (EC). The system has a preferred range of 0.5M—2M tetraalkylammonium salt and an electrolyte solvent containing about 15 to 85 volume % PC, 15 to 85 volume % (γ-BL) and 20 to 80 volume % EC. A most preferred ternary composition comprises a solution of 1M tetrabutylammonium hexaflourophosphate in 40 vol % PC, 30 vol % BL and 30 vol % EC found to combine very high conductivity and needed electrochemical stability. The most preferred tetraalkylammonium salt concentration is about 1M.

A preferred quaternary mixture includes γ-BL, EC, PC and dimethoxyethane (DME) in which the amounts of γ-BL and EC are roughly equal and the amounts of PC and DME are roughly equal and somewhat less than the γ-BL and EC. A most preferred quaternary solvent mixture using the above combines γ-BL, EC, PC and DME in the respective volume percent ratios of 30:30:20:20. The range of concentration of the tetraalkylammonium salt in the quaternary system is the same as for the ternary systems, i.e., 0.5M to 2M and preferably about 1M.

These aprotic solvent mixtures have fairly high dielectric constants and low viscosity that they can easily dissolve a stable tetraalkylammonium salt to give 1M solution with high conductivity and establish an electrochemical domain with a wide voltage window from −3.0 to +2.5 Volts. The electrolyte solutions are nontoxic, noncorrosive have high boiling points and low freezing points, have very low vapor pressure and have high solubility for gases and vapors.

The preferred sensor of the invention is a three electrode structure using a gold or platinum sensing electrode, a platinum counter electrode with a silver "quasi"-reference electrode or a platinum "pseudo"-reference electrode (both hereinafter referred to as reference electrodes) in combination with the electrolyte system of the invention. The cell is preferably operated using the technique of time variable scanning voltammetry in which the cell is subjected to an externally applied potential scan or time variable potential differential between the sensing electrode and the reference electrode in the allowable redox patented range using the technique of scanning voltammetry. This technique enables a variety of reducible and oxidizable toxic gases, toxic organic solvents and their vapors to be detected at very low concentrations. The sensing system has the capability for multi-gas/vapor sensing which has also been demonstrated.

BRIEF DESCRIPTION OF THE DRAWINGS

In the drawings wherein like numerals designate like parts throughout the same.

DETAILED DESCRIPTION

Certain embodiments of the detecting cell including the electrolytes and particularly certain preferred electrolytes in accordance with the invention will next be described. The embodiments detailed in the specification are introduced by way of example and not limitation and it is understood that other embodiments are contemplated and will occur to those skilled in the art. For example, other electrolytes and electrolyte combinations may be employed and other species detected.

Figure 4B:
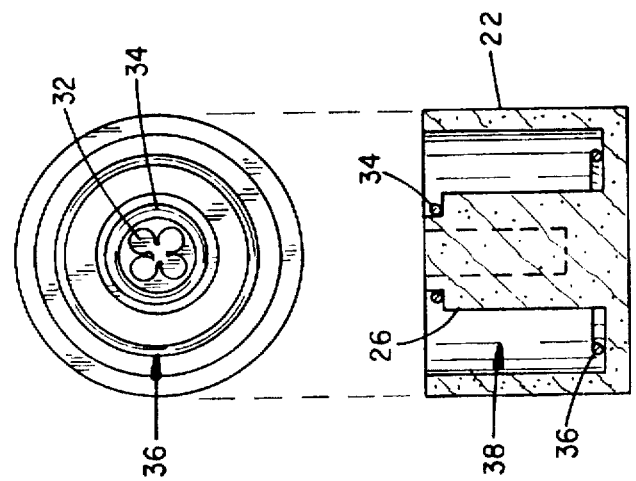
FIG. 4B depicts a plan in an exposed elevational view of the sensor of FIG. 4A.
Figure 4A:
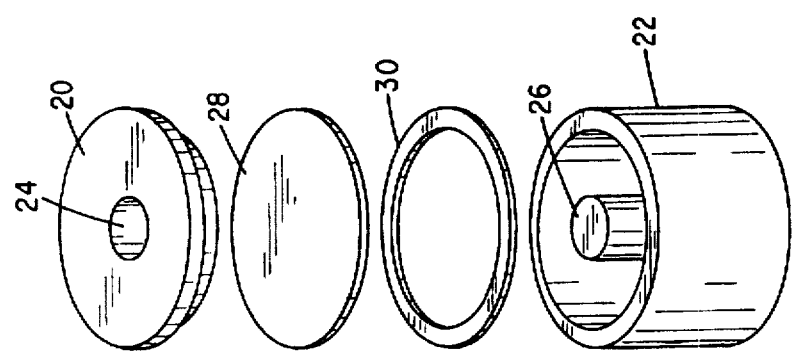
FIG. 4A depicts an exploded view of a cell in accordance with the sensor and in accordance with the invention.

FIGS. 4A and 4B generally illustrate an electrochemical cell embodiment in which a lid top 20 and a cell body 22 are machined from a readily machined ceramic material which may be Macor, or the like. The lid top 20 is provided with a central opening 24 and the cell body 22 is provided with a central cylindrical ceramic mound utilized for carrying electrodes as seen in FIG. 4B. A thickness (~50 microns) of a non-porous or micro-porous membrane, preferably of polytetrafluoroethylene (PTFE) is placed between the opening 24 and the cell body 22 and a gasket 30 seals the cell body 22 to the membrane 28. The gasket is preferably of rubber, but may be made of any benign resilient material chemically and physically compatible with the system of the invention.

The electrodes of the electrochemical sensor of the embodiment of FIG. 4A are depicted in FIG. 4B and include a working or sensing electrode 32 which may consist of several disc-shaped segments or fingers of gold or platinum. A platinum counter electrode 34 surrounds the sensing or working electrode 32 and it, in turn, is surrounded by a platinum or silver reference electrode 36 located in the cavity 38 surrounding the central ceramic mound 26. The cavity 38 defines an electrolyte reservoir and is designed to be filled with the electrolyte of the invention. The electrodes are made of gold, platinum or silver wires or films, as the case may be, deposited or otherwise placed in a well-known manner and the system is assembled in conjunction with suitable pads or wires for making electrical connections conventionally as required.

Figure 1:
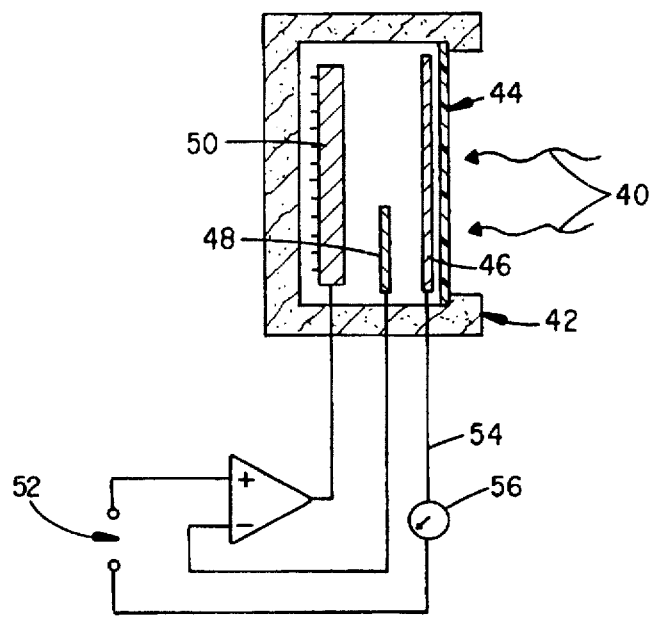
FIG. 1 is a schematic view of a sensor in accordance with the invention.
Figure 2:
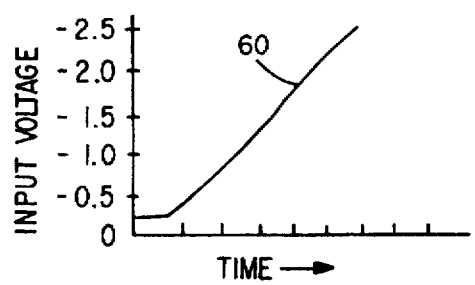
FIG. 2 illustrates linear scan voltammetry with respect to the input voltage applied to the cell in the schematic drawing of FIG. 1.
Figure 3:
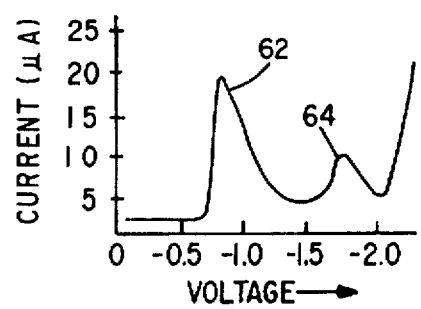
FIG. 3 illustrates multi-gas amperometric readings for $O_2$ and $CO_2$ based on a scanned input voltage of FIG. 2.

FIG. 1 schematically illustrates the sensing function of the sensor cell in which a gas or vapor 40 enters the cell 42 through a membrane 44 and thereafter encounters a sensing or working electrode 46. The system further includes reference electrode 48 and counter electrode 50, together with a conventional potentiostatic input voltage source 52 which is controlled by the help of the reference electrode 48 of the three electrode configurations. The current output on conductor 54 is indicative of the concentration of the species reduced and/or oxidized at the applied potential and may be measured as at 56 by suitable amperometric instrumentation in a well-known manner. The input voltage is applied by linear scanning voltammetry which is depicted graphically at 60 in FIG. 2. Note that the time scale is indeterminate indicating that the voltage can be ramped at any desirable rate to obtain proper measurements utilizing the cell. FIG. 3 shows typical current output recordings for gases depicting oxygen at 62 and carbon dioxide at 64 showing their characteristic redox voltages.

Figure 5:
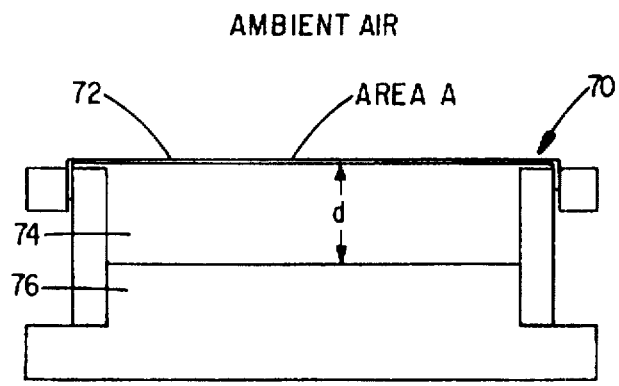
FIG. 5 depicts an elevational view of a possible sensor cell package in accordance with the invention.

FIG. 5 depicts another rudimentary cell schematic in conjunction with a gas sampling rate technique which can be utilized for improving the sensitivity and response time of the sensor. This is particularly applicable for monitoring very small concentrations (PPM levels) of toxic or irritant gases and organic vapors. In this case, the sensing system, generally at 70, includes a permeable/porous membrane 72 covering a chamber 74. The membrane is selected to be permeable to inorganic vapors of interest or porous to organic vapors of interest to be sensed, but is one that does not allow air currents into the chamber 74. The chamber 74, in turn, is adjacent to the electrochemical cell itself 76. Transport of gas molecules to the electrochemical cell is determined by the diffusion of the gas molecules and the diffusion process, in turn, is used to define a sampling rate which is independent of the ambient air conditions adjacent to the sensor cell. With reference to the figures, the sampling rate can be estimated by using an approximate value of the diffusion coefficient or constant "D" in conjunction with the area "A" of the sensor and the diffusion distance "d". Shown in conjunction with the figure, the sampling rate can be estimated by using the approximate value of the diffusion constant "D" at 0.04 cm$^2$/sec. A sensor area "A" of 5 cm$^2$ and a diffusion distance "d" equal to 0.5 cm gives a sampling rate of 25 cm$^3$/min. The corresponding response time for this system is given as approximately 8 seconds.

The aprotic non-aqueous electrolyte solvent combinations used in the cell are prepared by using ternary or quaternary solvent mixtures consisting of solvents with fairly high dielectric constants, high viscosity and high boiling points with generally low freezing points. Solvents belonging to this family include γ-butyrolactone (γ-BL), propylenecarbonate (PC), ethylenecarbonate (EC), dimethoxyethane, dimethyl carbonate, diethyl carbonate, ethyl acetate and other aprotic solvents. These solvents and solvent mixtures are generally used for high energy density lithium batteries and the solvents and their properties for the battery applications are described in greater detail in chapters 1 and 2 by the present inventor, H. V. Venkatasetty, in the Monograph Series "Lithium Battery Technology" edited by H. V. Venkatasetty and published by Wiley-Inter-Science, John Wiley & Sons, New York (1984).

While by no means limiting, highly purified solvents of PC, γ-BL and EC in ternary mixtures are generally most preferred and in the volume % ratios of PC 40: γ-BL 30: EC 30; or, in the same order, 30:40:30; or 30:30:40. In quaternary mixtures, the preferred constituents are γ-BL, EC, PC and dimethoxyethane (DME) and the most preferred ratios are 30:30:20:20, respectively by volume %.

For the electrolyte salt, pure tetraakylammonium salts have been used at 1M concentration and 1.5M concentration. Particular success in the combination of the invention has been achieved utilizing tetrabutylammonium hexafluorophosphate at 1M concentration.

The non-aqueous electrolyte solutions utilized in the sensor of the invention typically have room temperature conductivities in the range of about 7–15×10$^{-3}$ S/cm and electrochemical stability from about −3 to +2.5 Volts using gold and platinum sensing electrodes, and a platinum counter electrode and silver/platinum reference electrode. This wide voltage range covers the redox voltages of most gases and organic compounds of interest to environmental sensing, industrial process monitoring and control and medical diagnostics.

Examples of the compositions, composition solvent mixtures, and salt solutions for PC, EC and γ-BL that have been prepared are summarized in Table 1. Table 2 summarizes the conductivities of the salt solutions of Table 1.

TABLE 1

Compositions of Solvent Mixtures and Salt solutions prepared

| Solution type | PC:EC:-BL:Vol % | Salt type & Conc. |
| --- | --- | --- |
| A-1 | 40:30:30 | Tetrabutylammonium hexafluorophosphate at 1M. |
| A-2 | 50:20:30 | -same- |
| A-3 | 30:30:40 | -same- |
| B-1 | 40:30:30 | Tetrabutylammoniumhexafluorophosphate at 1.5M |
| B-2 | 50:20:30 | -same- |
| B-3 | 30:30:40 | -same- |
| J-1 | 30:00:70 | Tetrabutylammoniumhexafluorophosphate at 1M |
| J-2 | 40:00:60 | -same- |
| K | 40:30:30 | Tetraethylammonium perchlorate at 1M |
| L | 40:30:30 | Tetrabutylammonium perchlorate at 1M |

TABLE 2

Conductivities of electrolyte solutions measured.

| Solution type | Room temp. (25°) Conductivity in S/cm. × 10$^{-3}$ |
| --- | --- |
| A-1 | 8.993 |
| A-2 | 8.149 |
| A-3 | 8.595 |
| B-1 | 8.734 |
| B-2 | 8.23 |
| B-3 | 8.695 |
| J-1 | 8.058 |
| J-2 | 7.58 |
| K | 15.603 |
| L | 8.51 |

Experimentation used to develop sensors for environmental monitoring particularly of toxic Volatile Organic Compounds (VOCs) and carbon dioxide, and gases such as sulfur dioxide, nitrogen dioxide, hydrogen sulfide, ammonia and many others that have fairly high oxidation and/or reduction potentials required verification that the non-aqueous electrolyte solutions of the invention have the necessary stable electrochemical voltage window. The solutions of Table 1 were chosen particularly to evaluate their electrochemical stability for the voltage window of interest for detecting the gases of interest in accordance with the invention.

Accordingly, these solutions were placed in a three compartment cell separated by medium porosity disks. A platinum and/or a gold working electrode was placed in the central compartment, a platinum counter electrode and a silver quasi-reference electrode were placed in the other two compartments. The solutions were deaerated with dry argon gas. Linear scanning voltammetric studies were carried out in both the cathodic (reduction) and anodic (oxidation) range. The instrumentation used was modern laboratory type. The Princeton Applied Research Corporation Model 173 potentiostat/galvanostat with a model 175 Universal Programmer with Keithly Autoranging multimeters and interfaced with a McIntosh computer to control the experimental parameters, data collection, data reduction and storage were used throughout the experimental work.

In the case of solutions of ternary solvent mixtures containing tetrabutylammonium hexafluorophosphate with gold working electrode, cathodic linear scanning voltammetry was run from 0 to −2.4 V vs Ag and on the anodic scanning was run from 0 to 30 1.8 V vs Ag. In the case of platinum working electrode on the cathodic side, linear scanning voltammetry was run from 0 to −2.2 V vs Ag and on the anodic side, it was run from 0 to +2.0 V vs Ag. All these scanning studies were conducted at a scan rate of 50 mV/second unless otherwise stated. The voltage at which the current increases rapidly was taken as the voltage limit for that particular solution. These linear scanning voltammetric experiments were also run using platinum pseudo-reference electrode to evaluate the applicability of platinum reference electrode in these measurements, particularly in hardware Prototype cells because of ease of manufacturing of electrode structures in one operation on an insulating substrate by sputter deposition technique.

Linear scanning voltammetry of solution #K, containing 1M solution of tetraethylammonium perchlorate in the solvent mixture of PC, EC and γ-BL with gold working electrode, platinum counter and platinum and/or silver reference electrode shows a stable current-voltage curve on the cathodic side from 0 to −1.5 V vs platinum and/or silver. With platinum working electrode, platinum counter and platinum and/or silver reference electrode, linear scanning voltammetry on the cathodic side shows a voltage window from 0 to −1.5 V. On the anodic side, the voltage window extends very slightly to +1.7 V. Therefore, even though the conductivity of this solution is quite high compared to those of other electrolyte solutions, the voltage window for reduction and/or oxidation based sensing applications is limited and not suitable for multigas sensing and sensing organic vapors.

Linear scanning voltammetry of solution #L, containing 1M solution of tetrabutylammonium perchlorate further showed that on the cathodic side with gold working electrode, the voltage window extends from 0 to −2.1 V vs Ag and with platinum working electrode, the voltage window is from 0 to −1.6 V vs Ag and from 0 to −2 V vs pt. On the anodic side, with gold working electrode, the voltage window is from 0 to +1.8 V vs Ag and with platinum electrode, the voltage window is from 0 to +2 V vs Ag. Even though the electrochemical voltage window for solution #L is acceptable, the conductivity of this solution was too low to be suitable. The available electrochemical voltage window for reduction and oxidation reactions of these solutions in various solvent mixtures are summarized in Table 3.

Overall considerations of electrolytic conductivity and the electrochemical voltage stability window have led to the conclusion that solution #A-1, namely 1M solution of tetrabutylammonium hexafluorophosphate in a three solvent mixture being evaluated as the most preferred solution.

Figure 6:
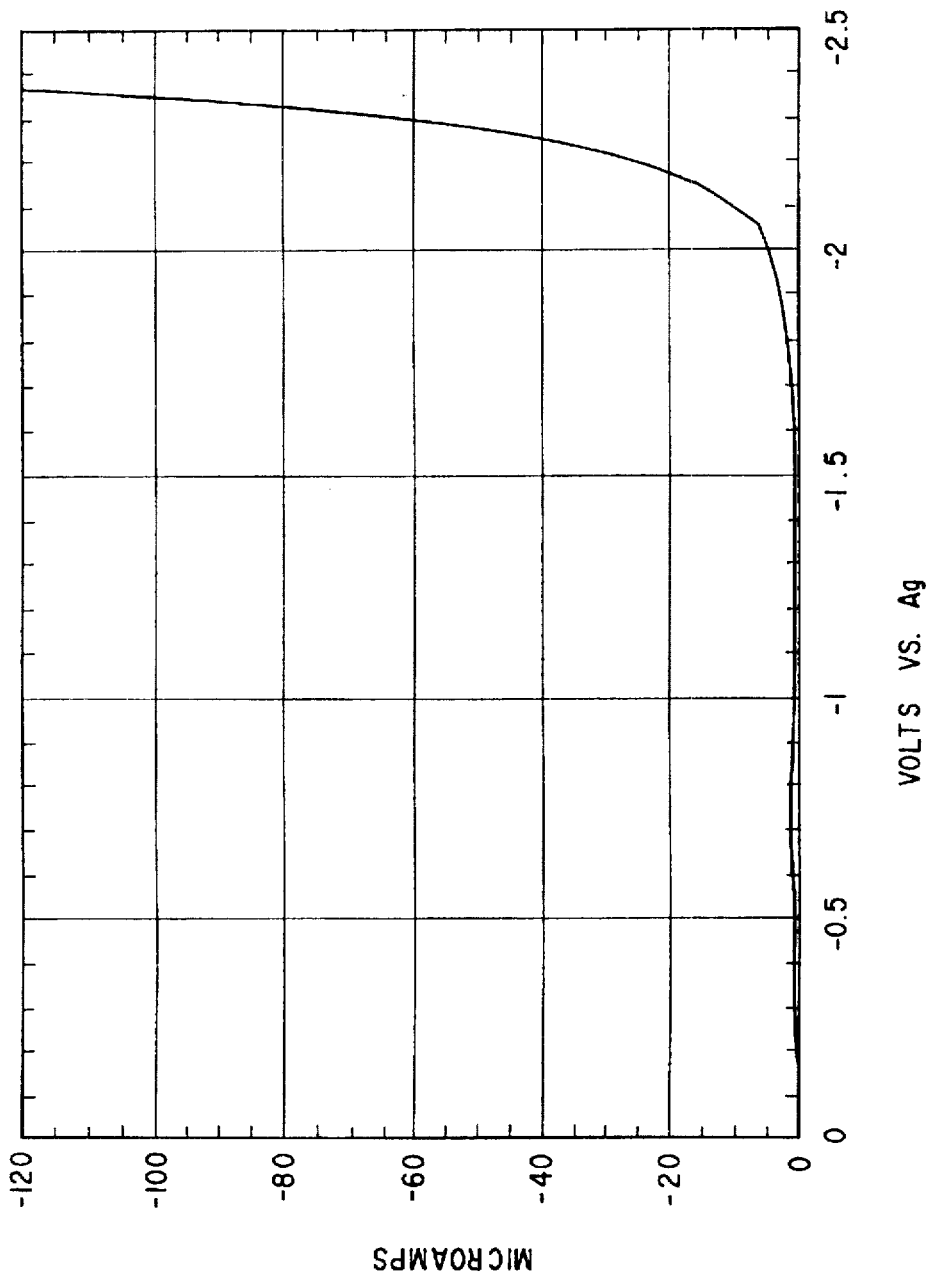
FIG. 6 is a baseline plot of a three electrode cell with an electrolyte system of 1M tetrabutylammonium hexafluorophosphate in 40 vol % PC, 30 vol % γ-BL and 30 vol % EC utilizing the cell having a platinum counter electrode, a gold working or sensing electrode and a silver reference electrode.
Figure 8:
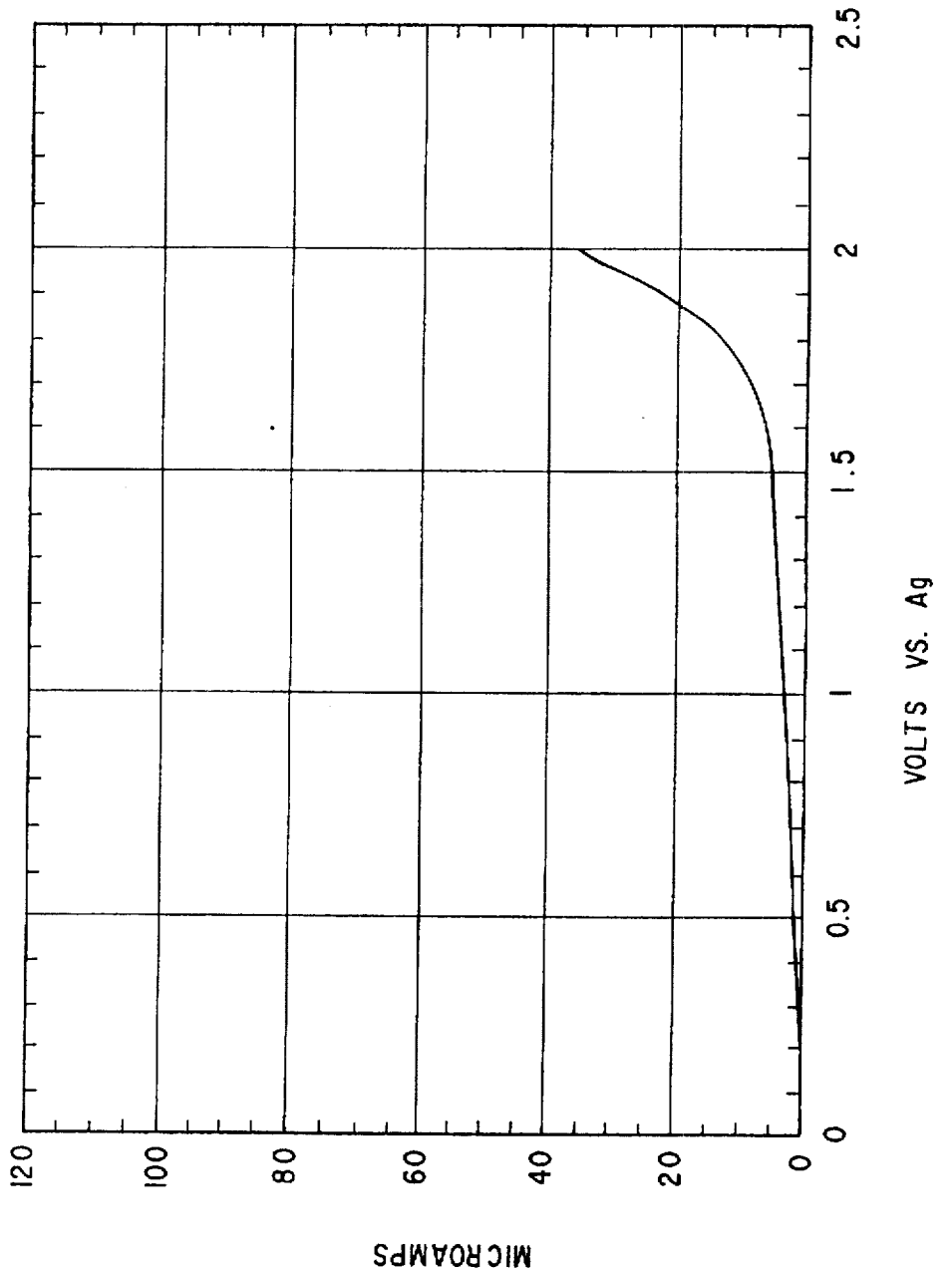
FIG. 8 is a baseline plot of a sensor similar to that of FIG. 6 wherein the working or sensing electrode is platinum.
Figure 9:
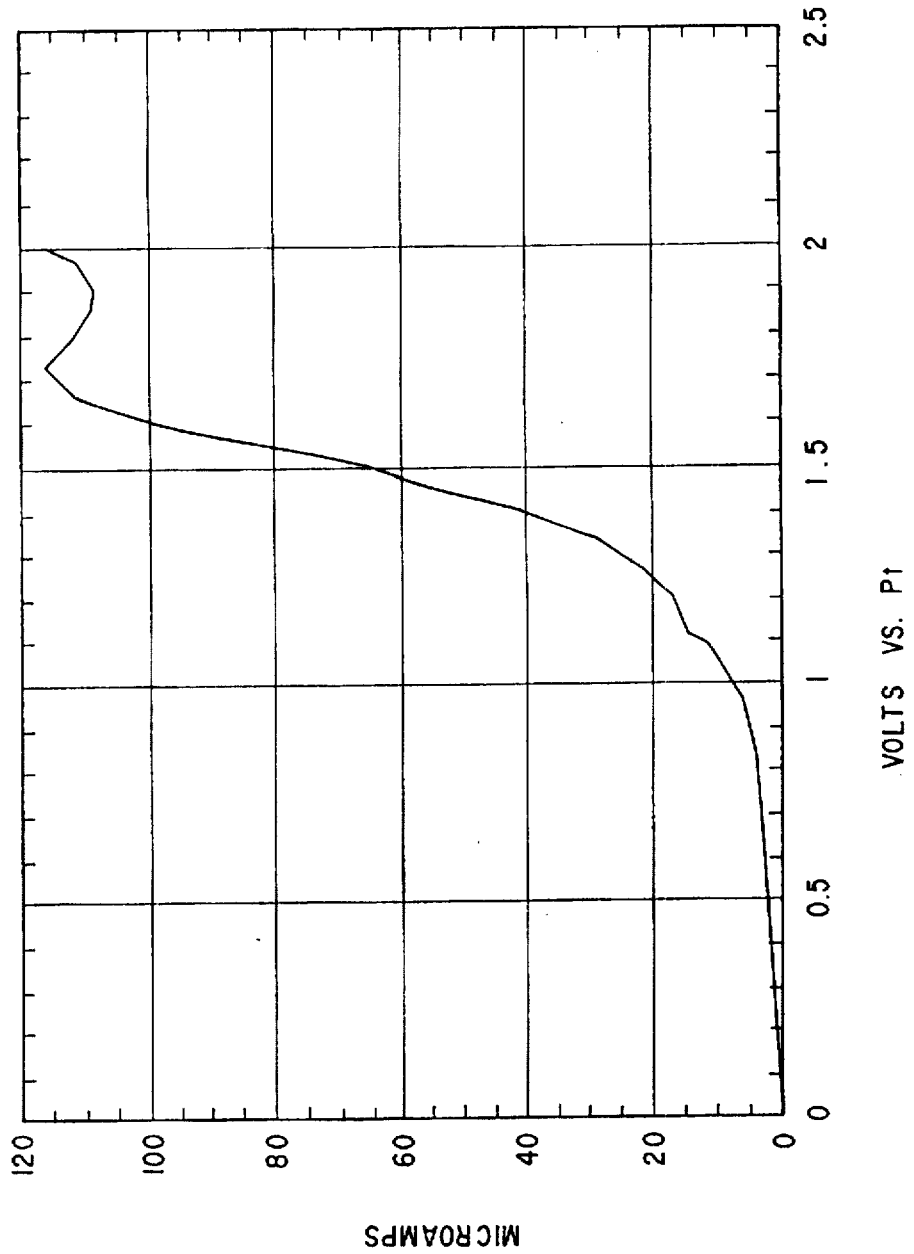
FIG. 9 illustrates the response of a similar cell having all platinum electrodes in accordance with the invention to trichloroethylene ($CHCCl_3$)
Figure 10:
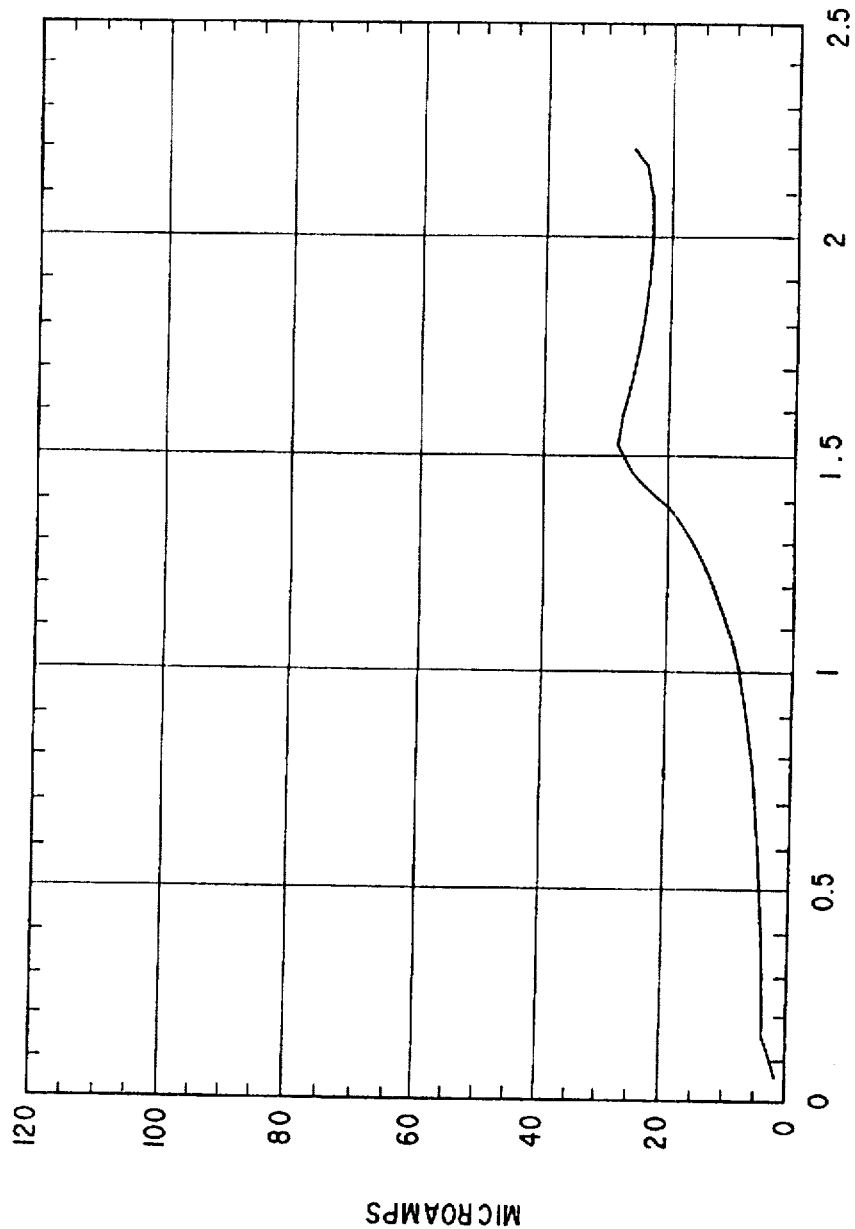
FIG. 10 is a further plot illustrating the response of the sensor of FIG. 9 to dichloromethane ($CH_2Cl_2$)
Figure 11:
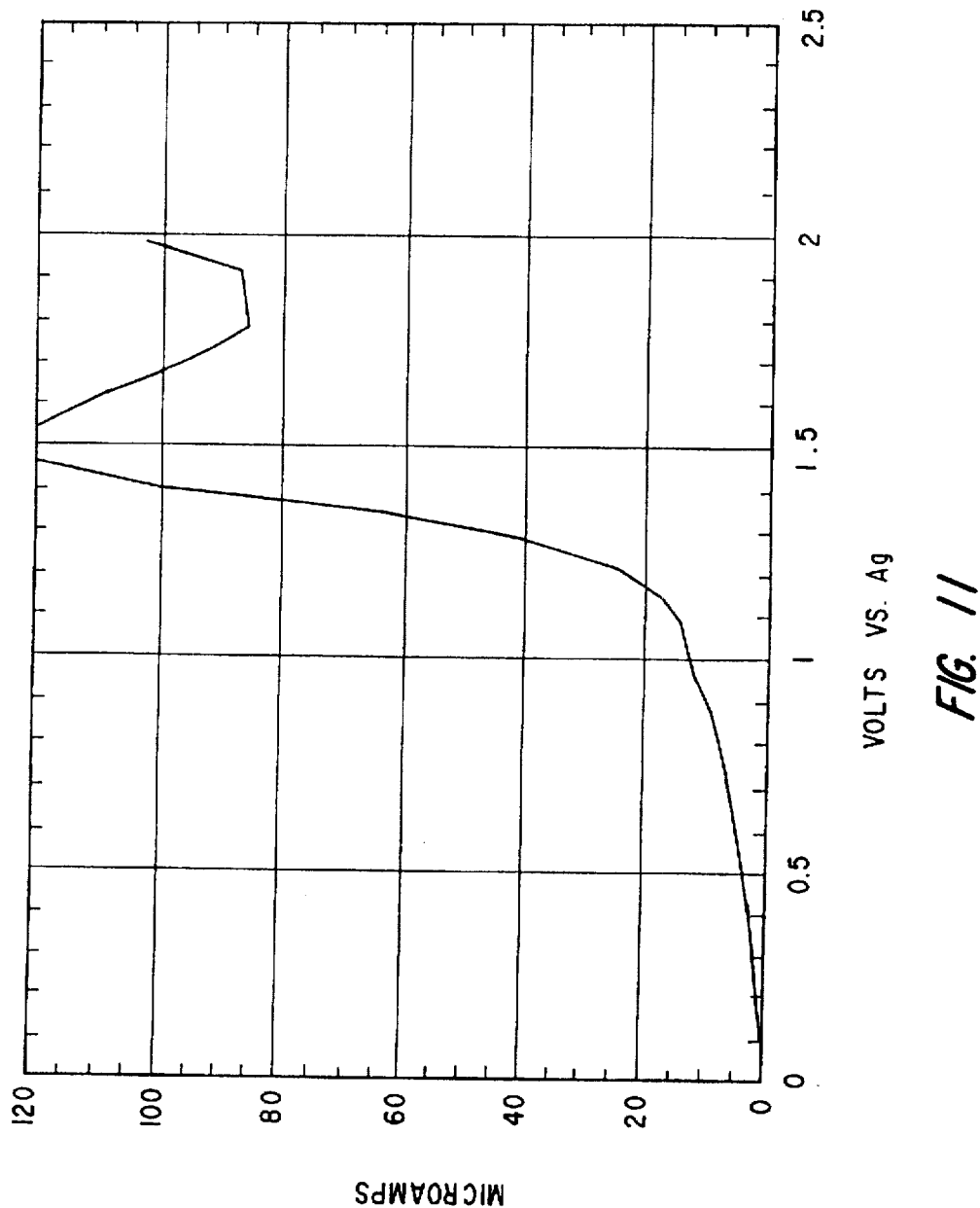
FIG. 11 is a plot of the reaction of the cell of FIG. 8 to chloroform ($CHCl_3$)
Figure 12:
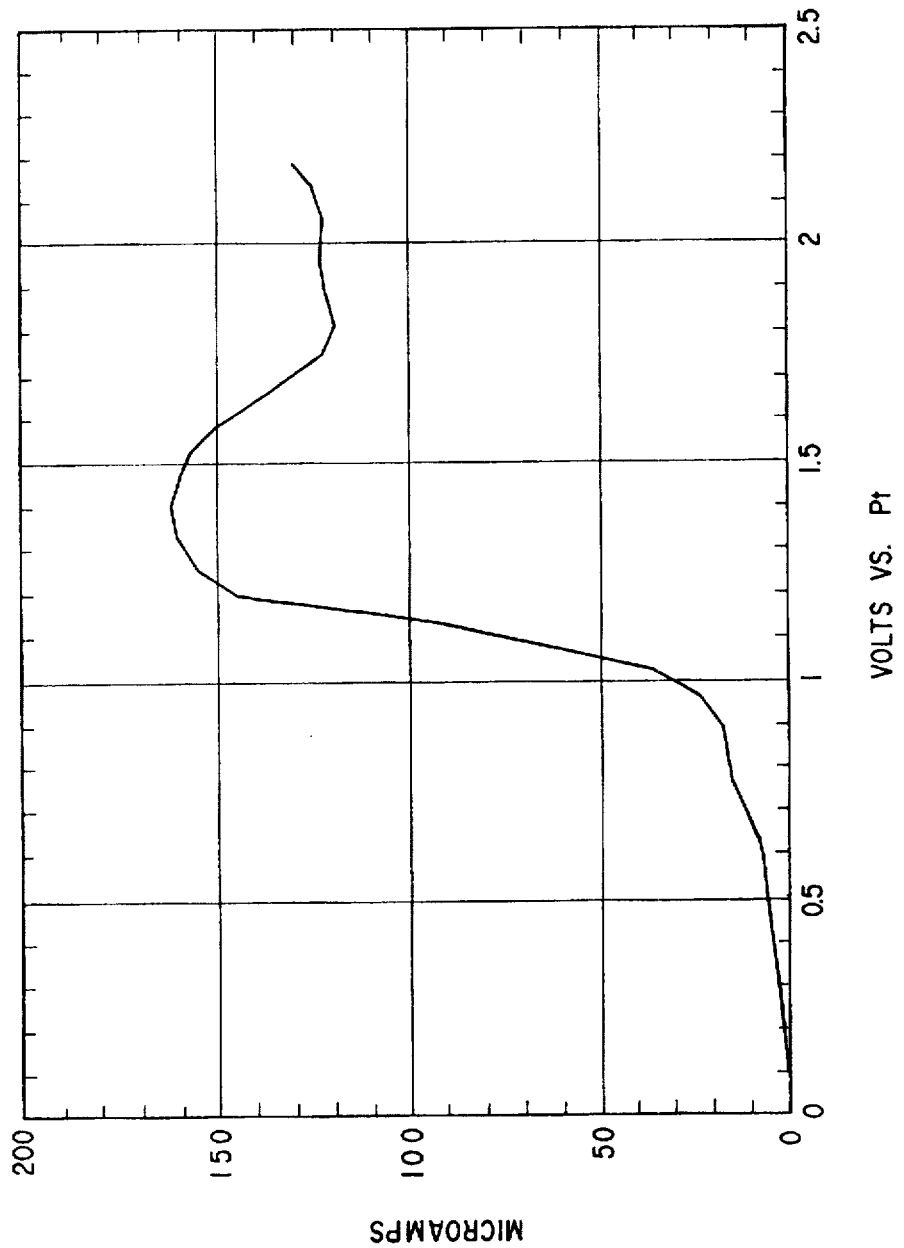
FIG. 12 illustrates the reaction of a cell as in FIG. 9 or 10 to carbontetrachloride ($CCl_4$)
Figure 13:
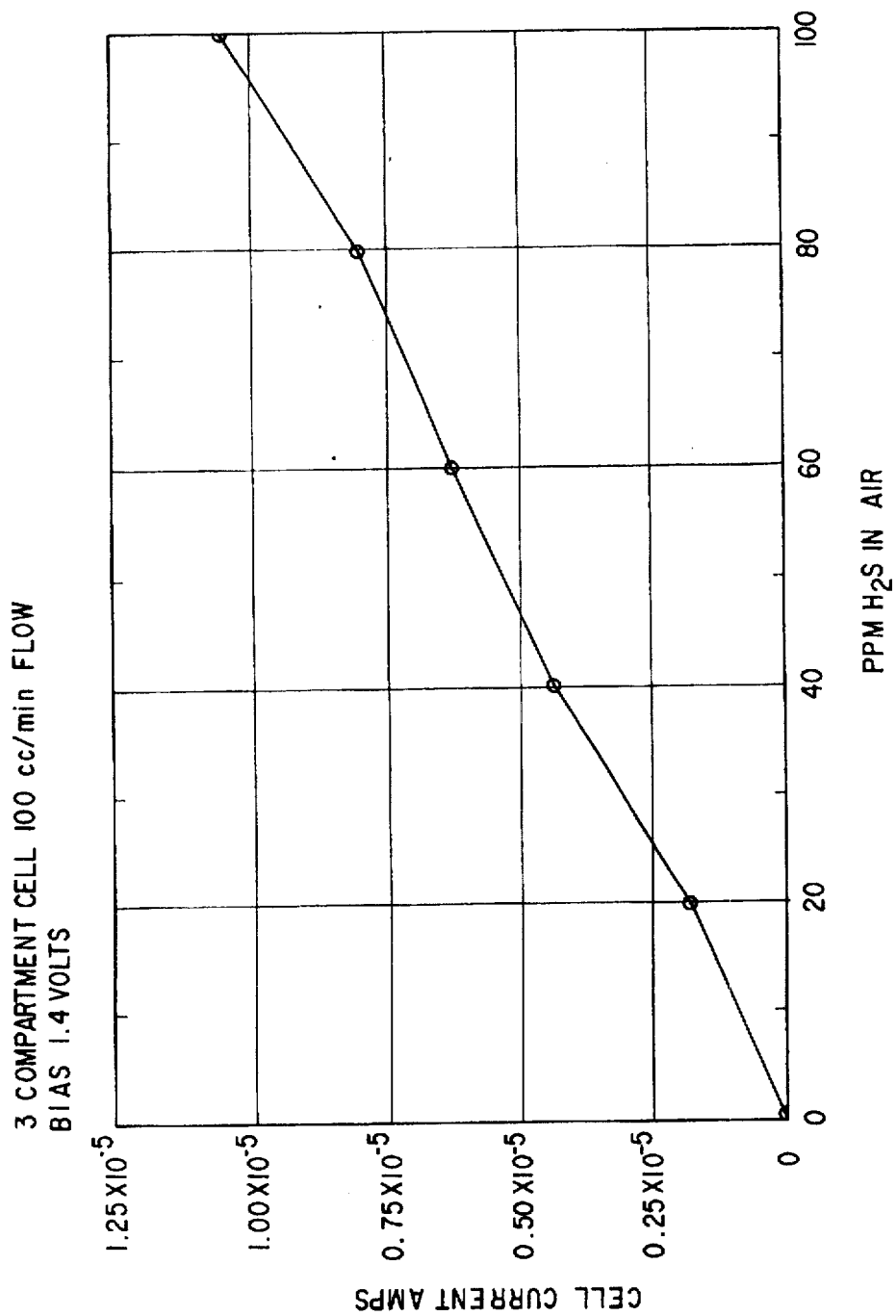
FIGS. 13–15 show the detection of 10 to 100 PPM respectively of hydrogen sulfide ($H_2S$), sulfur dioxide ($SO_2$) and nitrogen dioxide ($NO_2$)

Accordingly, FIGS. 6 and 8 depict baseline plots for solution A-1. FIG. 6 depicting the cathodic voltage range of an Au electrode vs Ag up from 0 to about −2.3 V and in FIG. 8 depicts the anodic voltage range for Pt vs Ag of 0 to about 2 V.

TABLE 3

Summary of Electrochemical Voltage Window of Solutions Measured

| Electrolyte solution type | Cathodic voltage range | Anodic voltage range |
| --- | --- | --- |
| A-1 | Au electrode vs Ag 0 to −2.3 V | Au electrode vs Ag. 0 to +1.8 V |
| | Au vs Pt. 0 to −2.2 | Au vs Pt 0 to +1.8 V |
| | Pt electrode vs Ag 0 to −2.2 V | Pt vs Ag 0 to 2 V |
| | Pt. vs Pt. 0 to −2 V | Pt. vs Pt 0 to +1.8 V |
| A-2 | Au electrode vs Ag 0 to −2.2 V | Au electrode vs Ag 0 to +1.8 V |
| | Au vs Pt. 0 to −2.2 V | Au vs Pt. 0 to +1.8 V |
| | Pt. vs Ag 0 to −2.2 V | |
| | Pt. vs Pt. 0 to −1.8 V | |
| A-3 | Pt. electrode vs Pt. 0 to −2.2 V | Pt. electrode vs Pt. 0 to +1.7 V |
| B-1 | Au electrode vs Pt. 0 to −2 V | Au electrode vs Pt. 0 to +1.8 V |
| | Au vs Ag 0 to −2.1 V | |
| B-2 | Au electrode vs Pt. 0 to −2.2 V | Pt. electrode vs Pt. 0 to +1.5 V |
| | Pt. vs Pt. 0 to −1.7 | |
| B-3 | Au electrode vs Ag 0 to −2.2 V | Pt. electrode vs Pt. 0 to +1.6 V |
| | Au vs Pt. 0 to −2.2 V | |
| J-1 | Au electrode vs Ag. 0 to −2.2 V | Au electode vs Pt. 0 to +1.8 V |
| | Au vs Pt. 0 to −2.4 V | |
| J-2 | Au electrode vs Ag 0 to −2.4 V | — |
| K | Au electrode vs Pt. 0 to −1.5 V | Pt. electrode vs Pt. 0 to +1.7 V |
| | Pt. vs Pt. 0 to −1.5 V | |
| L | Au electrode vs Ag 0 to −2.1 V | Au electrode vs Ag 0 to +1.8 V |
| | Pt. vs Ag. 0 to −1.6 V | Pt. vs Ag 0 to +1.9 V |
| | Pt. to Pt. 0 to −2 V | |

Figure 7:
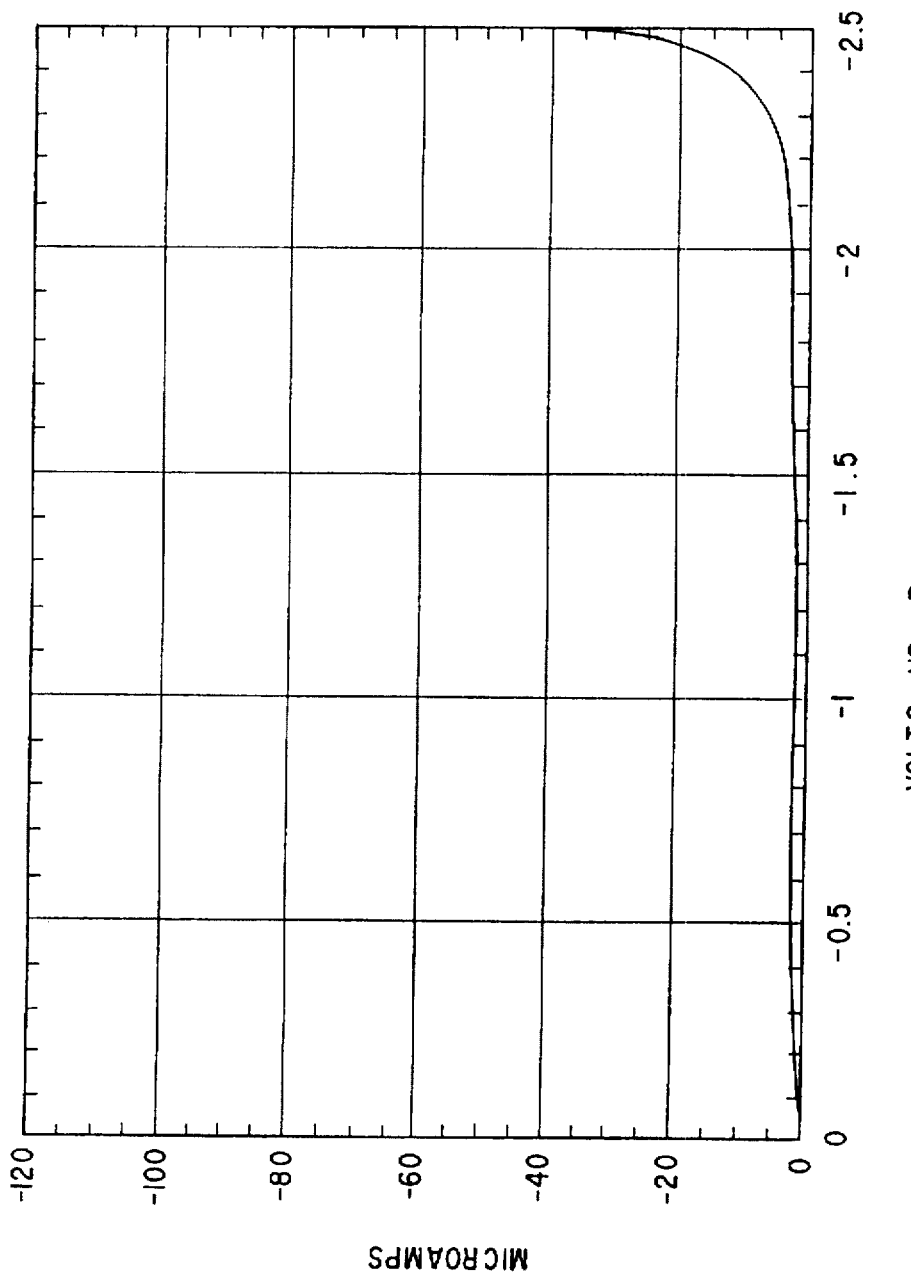
FIG. 7 is a baseline plot of a sensor similar to that of FIG. 6 wherein the reference electrode is platinum.

FIG. 7 depicts a baseline plot of Au V Pt for the cathodic voltage range of 0 to about −2.4 V.

FIGS. 9–12 show characteristic responses of cells utilizing electrolyte solution type A-1 to detect variety of organic species including trichloroethylene dichloromethane, chloroform and carbontetrachloride.

Figure 14:
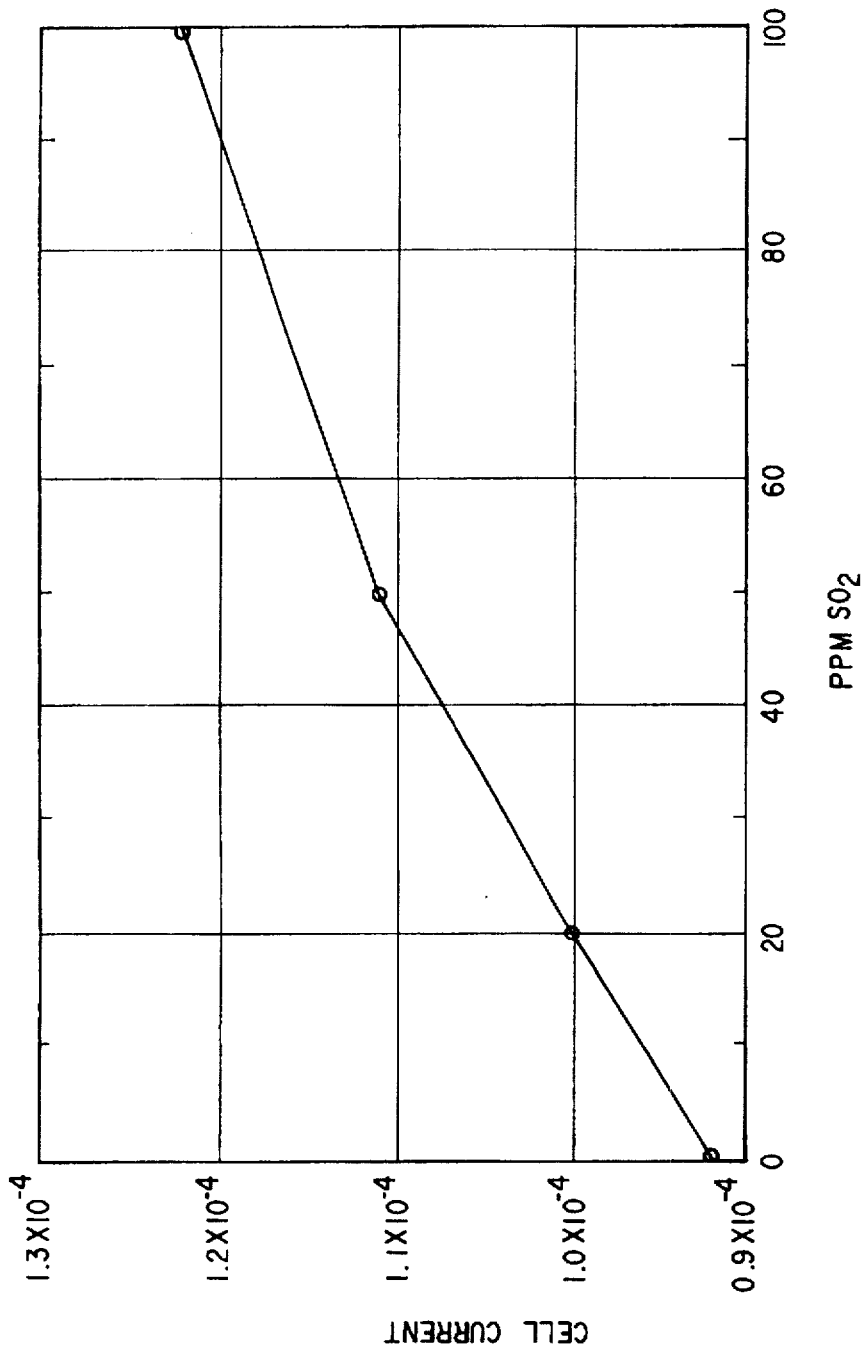
Figure 15:
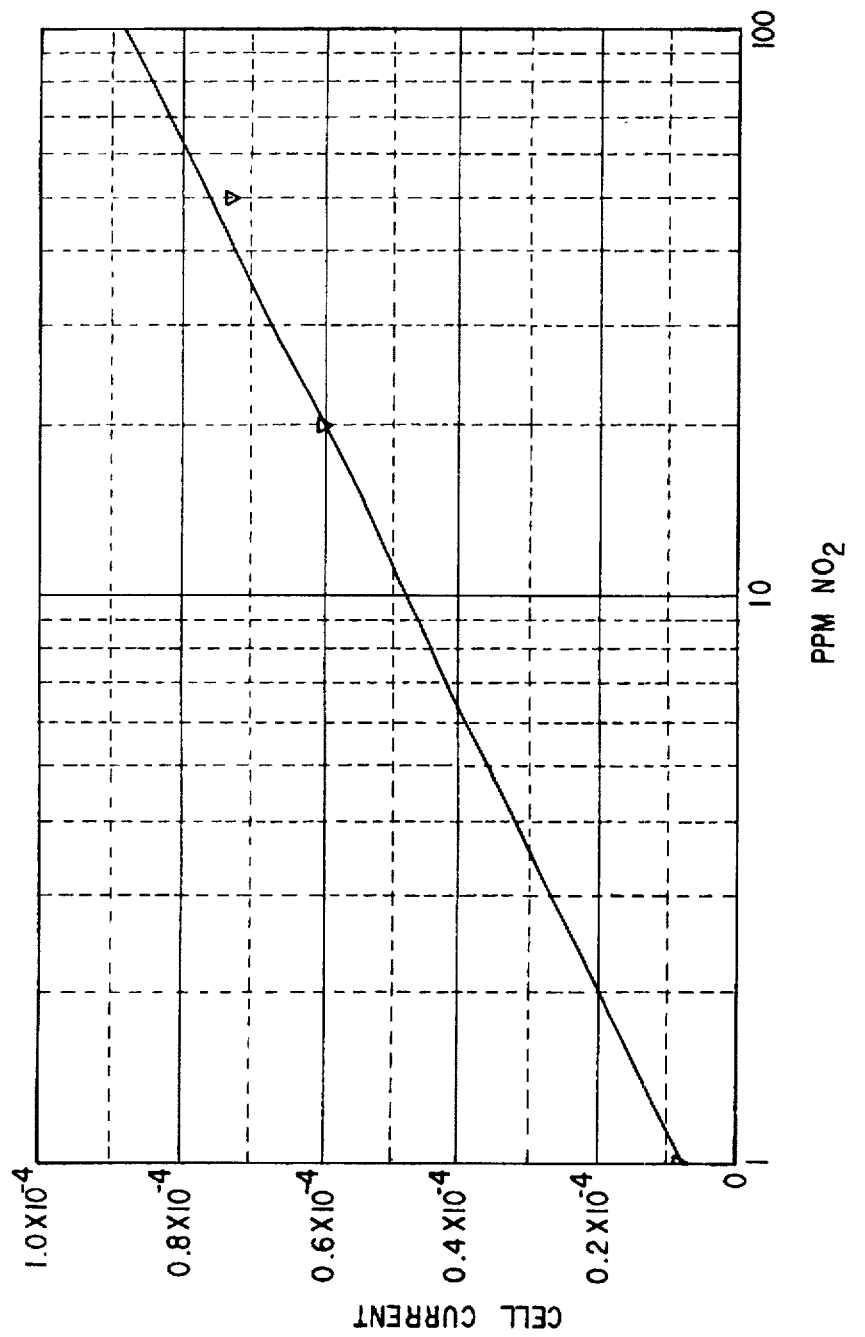
Figure 16:
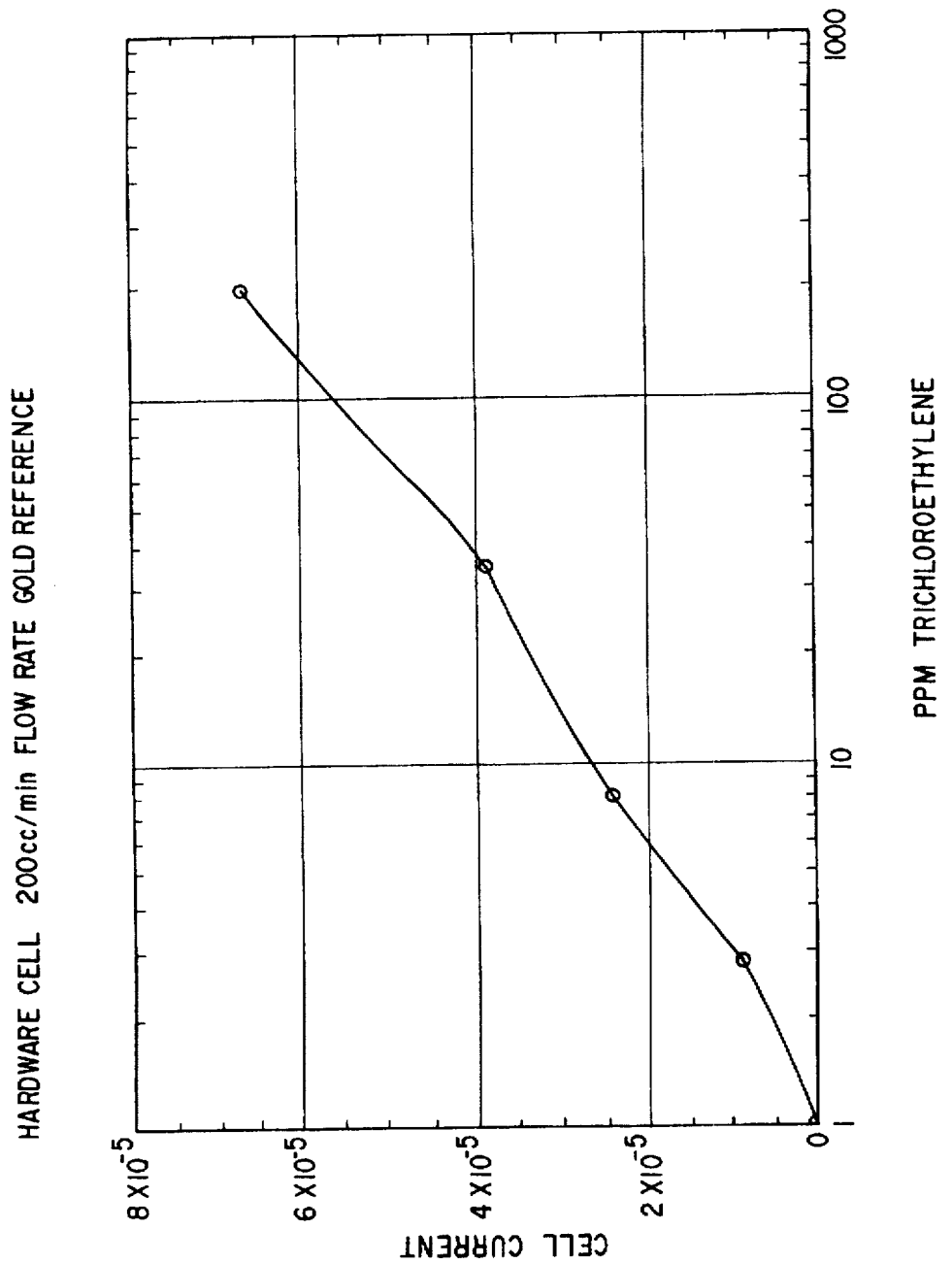
FIG. 16 shows the detection of levels of 5 to 100 PPM of trichloroethylene ($CHCCl_3$)
Figure 17:
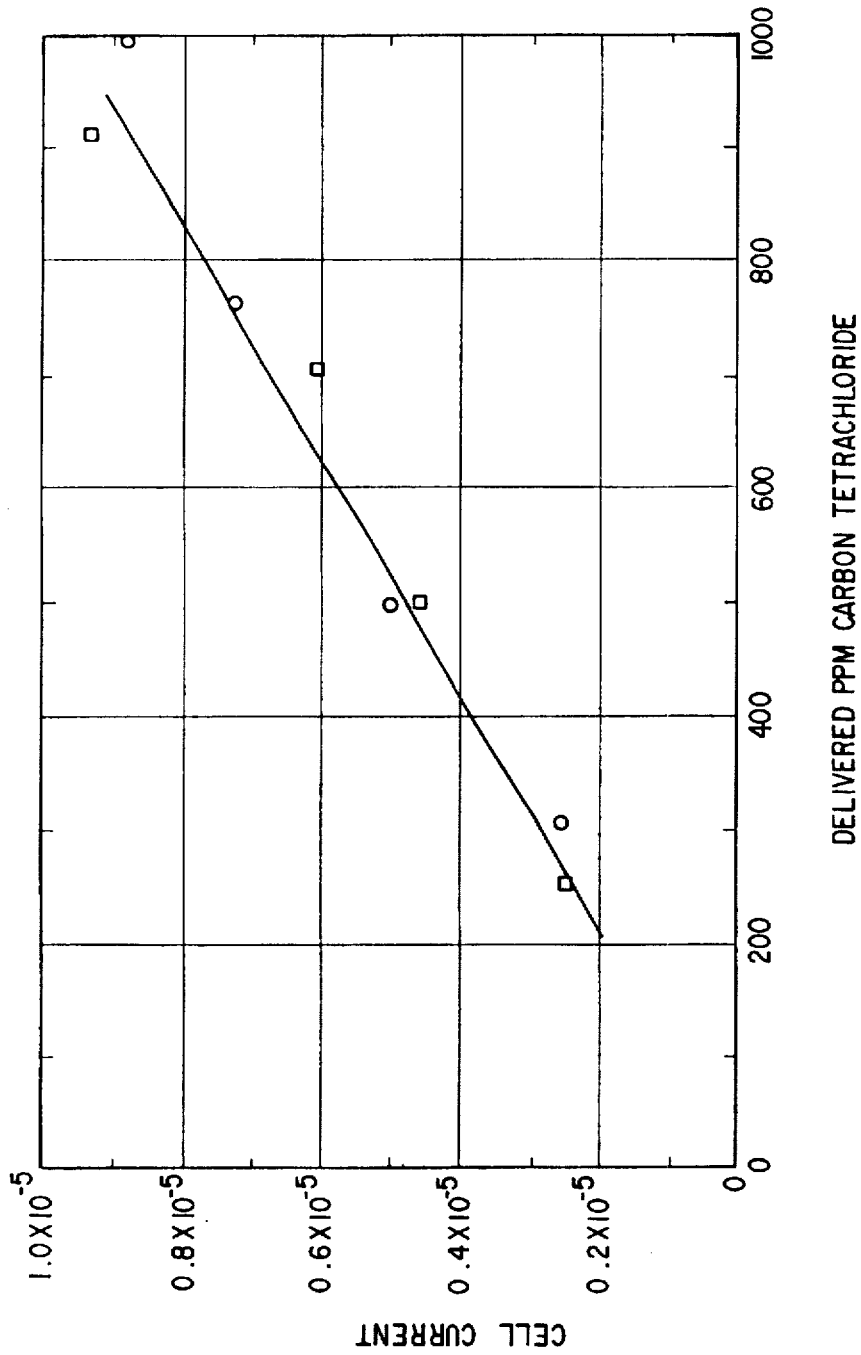
FIG. 17 depicts the detection levels of 200 to 1000 PPM of carbontetrachloride ($CCl_4$)
Figure 18:
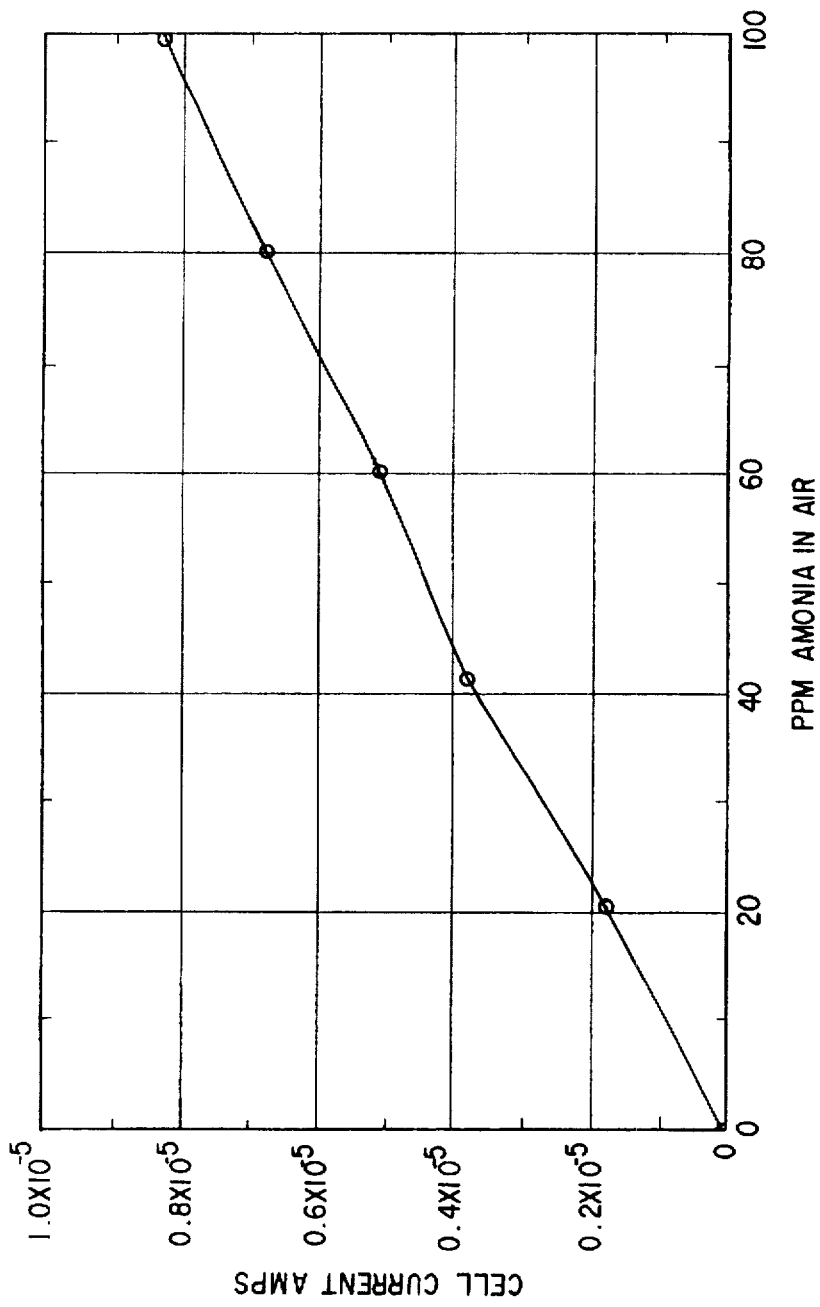
FIG. 18 depicts the detection of 0–100 PPM of ammonia.

FIGS. 13–18 show the characteristic response curves for low concentrations of certain toxic species utilizing the three compartment cells and prototype cells at various sampling rates. (The sampling rate of FIG. 14 is not shown.)

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

In the claims:

I claim:

1. A system for sensing gaseous species of interest comprising:

(a) an electrochemical sensor for sensing sampled gaseous species of interest, the sensor comprising:
  i. a sensing electrode selected from the group of materials consisting of platinum and gold;
  ii. a platinum counter-electrode;
  iii. reference electrode consisting of a material selected from silver and platinum; and
  iv. a mixed solvent based aprotic non-aqueous electrolyte comprising an aprotic organic solvent mixture containing solvents selected from the group consisting of γ-butyrolactone, ethylene carbonate, propylene carbonate, dimethoxy ethane, dimethyl carbonate, ethyl acetate and diethyl carbonate and an amount of a stable, non-hygroscopic tetraalkylammonium salt in said solvent; and (b) an air sampling diffusion chamber associated with said electrochemical sensor, said diffusion chamber comprising:
  i. a sidewall enclosing a known diffusion area and having a known height, thereby describing a diffusion chamber having two ends;
  ii. a sample diffusion membrane selected from the group consisting of gas permeable and micro porous membranes and combinations thereof for contacting the environment closing one of said ends of said diffusion chamber;
  iii. wherein a second end of said diffusion chamber is exposed to and closed by said electrochemical cell a selected distance from said diffusion membrane thereby defining a diffusion chamber depth; and
  iv. wherein said known diffusion area and chamber depth dimensions of said sampling diffusion chamber and diffusion coefficient of a gas of interest define a set sampling rate for said electrochemical cell with respect to said gas of interest.

2. The system of claim 1 wherein said tetraalkylammonium salt is tetrabutylammonium hexafluorophosphate.

3. The system of claim 2 wherein the concentration of said tetrabutylammonium hexafluorophosphate is between about 0.5M and 1.5M.

4. The system of claim 3 wherein the concentration of said tetrabutylammonium hexafluorophosphate is 1M.

5. The system of claim 4 wherein said electrolyte solution comprises:

propylene carbonate about 30% by volume

γ-butyrolactone about 30% by volume ethylene carbonate about 20% by volume dimethoxyethane about 20% by volume.

6. The system of claim 1 wherein said electrolyte solution comprises γ-butyrolactone, ethylene carbonate and propylene carbonate.

7. The system of claim 6 wherein said electrolyte solvent contains from about 30% to 40% by volume of γ-butyrolactone; from about 30% to about 40% by volume ethylene carbonate and from about 30% to about 40% by volume propylene carbonate.

8. The system of claim 6 wherein said electrolyte solvent further comprises an amount of dimethoxyethane.

9. The system of claim 8 wherein said electrolyte solution comprises:

propylene carbonate about 30% by volume

γ-butyrolactone about 30% by volume ethylene carbonate about 20% by volume dimethoxyethane about 20% by volume.

10. The system of claim 9 further comprising means for applying a scanning voltage between said sensing electrode and said reference electrode.

11. The system of claim 1 wherein said sampling rate is designed for a gas of interest by adjusting one or more of the group consisting of the diffusion area of the diffusion chamber and the diffusion chamber depth.

12. The system of claim 11 wherein said solvent mixture consists of approximately 30% by volume γ-butyrolactone; 30% (vol) ethylene carbonate and about 40% by volume propylene carbonate.

13. The system of claim 11 further comprising a device for applying a scanning voltage between said sensing electrode and said reference electrode.

14. The system of claim 1 further comprising a device for applying a scanning voltage between said sensing electrode and said reference electrode.

15. The system of claim 14 wherein said solvent mixture consists of approximately 30% by volume γ-butyrolactone; 30% by volume ethylene carbonate and about 40% by volume propylene carbonate.

16. The system of claim 14 wherein said device for applying a scanning voltage includes a means for applying at a set rate.

17. A method of sampling and sensing a sampled gaseous species of interest comprising the steps of:

(a) providing an electrochemical cell sensor having an electrode system and an electrolyte system sensitive to the gas of interest;

(b) providing a sampling diffusion chamber having a sidewall enclosing a known diffusion area and having a known height and two ends, one of which is closed by said electrochemical cell, the other end being closed by a sample diffusion membrane of known permeability for the gas of interest at a known diffusion distance from said electrochemical cell;

(c) varying the relationship among the diffusion area, diffusion distance and permeability to adjust the sampling rate for the gas of interest; and (d) employing said adjusted sampling rate for sensing said gas of interest.

* * * * *